United States Patent [19]

Fukui et al.

[11] Patent Number: 4,906,582
[45] Date of Patent: Mar. 6, 1990

[54] EMISSION ANALYSIS METHOD WITH INDUCTIVELY-COUPLED RADIO FREQUENCY PLASMA AND APPARATUS FOR USE IN SUCH METHOD

[75] Inventors: Isao Fukui, Uji; Koji Okada, Kyoto, both of Japan

[73] Assignee: Shimadzu Corporation, Kyoto, Japan

[21] Appl. No.: 256,404

[22] Filed: Oct. 6, 1988

Related U.S. Application Data

[63] Continuation of Ser. No. 27,450, Mar. 18, 1987, abandoned.

[30] Foreign Application Priority Data

Mar. 18, 1986 [JP] Japan ..................... 61-61555

[51] Int. Cl.$^4$ ................. G01N 21/71; G01N 27/00
[52] U.S. Cl. ............................. 436/153; 422/98
[58] Field of Search ............. 356/315, 316; 422/54, 422/98; 436/153, 154, 35

[56] References Cited

U.S. PATENT DOCUMENTS

4,575,609  3/1986  Fassel et al. .............. 356/316 X
4,636,339  1/1987  Kenney .................... 356/316 X

OTHER PUBLICATIONS

Black et al.; Volatile Metal–Chelate Sample Introduction for Inductively Coupled Plasma–Atomic Emission Spectrometry; Anal. Chem., 53(2), 1981, pp. 249–253.
Kamiya et al.; Inductively-Coupled Plasma (ICP) Emission Spectrometry; CA 105(6):53801e, 1985.

*Primary Examiner*—Barry S. Richman
*Assistant Examiner*—T. J. Wallen
*Attorney, Agent, or Firm*—Birch, Stewart, Kolasch & Birch

[57] ABSTRACT

An analyzing method of an Inductively-Coupled Radio Frequency Plasma (ICP) apparatus including a switch valve means for switching the flow of a sample which comprises the steps of: first switching the switch valve to the side of a plasma torch only during an ICP analyzing time; first supplying an induction coil a first radio frequency electric power and the plasma torch first volume of gas to cause plasma; analyzing the plasma; second switching the switch valve to an exit side of the sample during the times except for the ICP analyzing time; and second supplying the induction coil a second radio frequency electric power and the plasma torch second volume of gas to keep pilot light plasma, and an apparatus for use in such method; whereby the plasma is maintained at a condition of a pilot light except for analyzing, and a running cost is reduced.

7 Claims, 3 Drawing Sheets

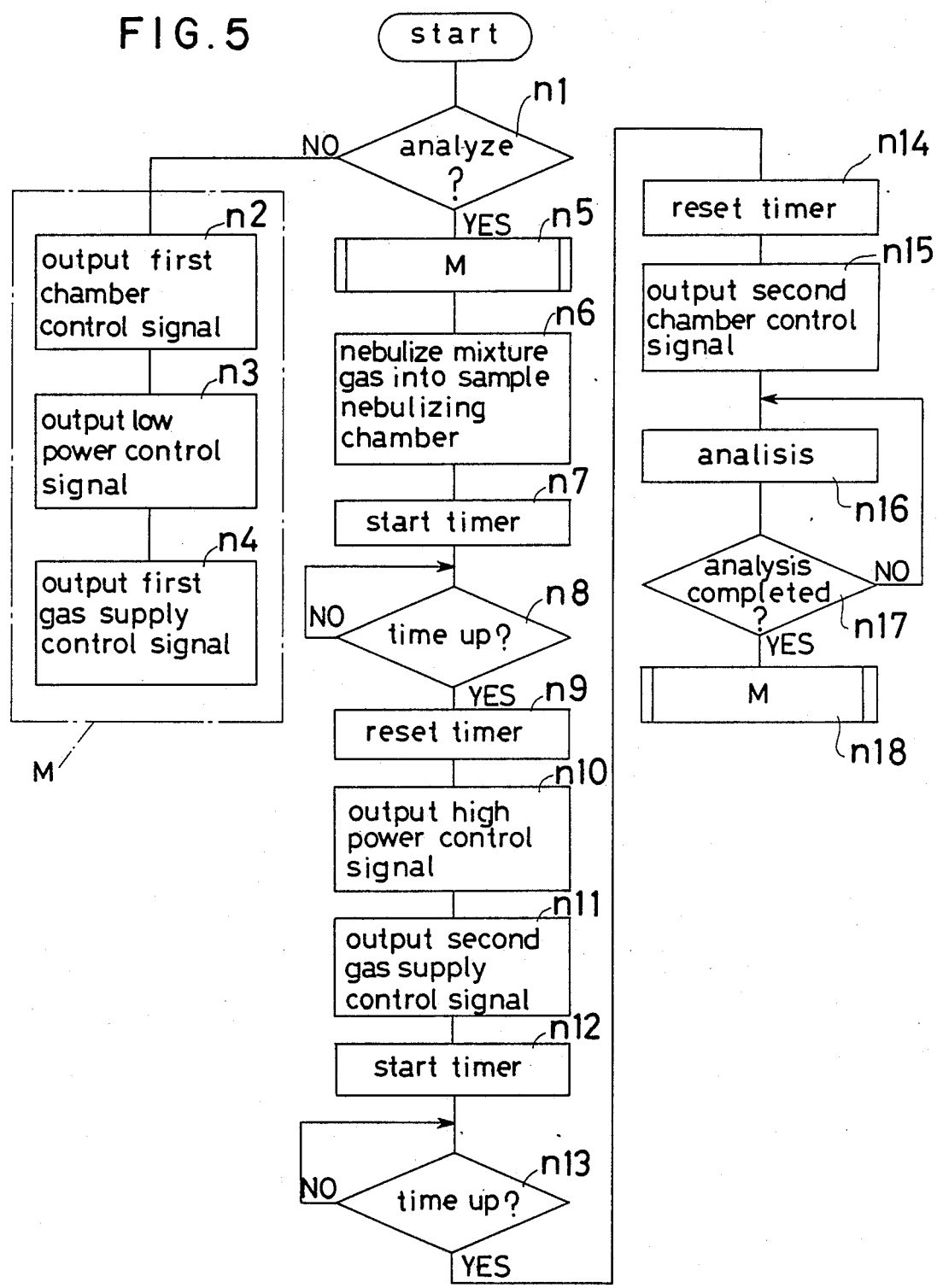

EMISSION ANALYSIS METHOD WITH INDUCTIVELY-COUPLED RADIO FREQUENCY PLASMA AND APPARATUS FOR USE IN SUCH METHOD

This application is a continuation, of application Ser. No. 07/027,450 filed on Mar. 18, 1987, now abandoned.

BACKGROUND OF THE INVENTION

The present invention relates to an emission analysis method with an inductively-coupled radio frequency plasma as a source for emission analysis and an apparatus for use in such method and, more particularly, to an emission analysis method with an inductively-coupled radio frequency plasma as a source for emission analysis and an apparatus for use in such method to reduce a running costs.

Emission analysis is used when a sample is exposed to electrical or thermal energy, whereby, the spectra of emitted light from the sample are analysed by a spectroscope to obtain the spectra peculiar to elements contained in the sample. The presence and the strength of the spectra are measured to perform quantitative or qualitative analysis of the elements in the sample. In particular, an inductively-coupled radio frequency plasma (referred to as an ICP hereinafter) is suitable for performing the quantitative or qualitative analysis of a soldered sample as a source.

As a high frequency plasma for a source, the ICP is characterized in that a high frequency current less than 300M Hz flows through a coil to cause a high frequency magnetic field. According to the change of the high frequency magnetic field, an electromagnetic induction field is caused to discharge, whereby the combination of the discharge and an electric circuit becomes inductive. A light source of this type is called an ICP.

As compared with a spark or arc method as a source for emission analysis, the ICP system can afford a stable plasma and high precision of analysis. Conventionally, to maintain the stable generation of the plasma or continuously analyse a plurality of samples, a sample inlet system should be stabilized for each of the samples. Therefore, a gas inlet system to a plasma torch and a high frequency voltage source for generating a high frequency magnetic field are continuously operated in an appropriate analysis condition even without analysis taking place. It takes about 10-20 seconds to introduce a new sample into a plasma torch and analyze it. In comparison with the time necessary for analysis, the time necessary for stabilizing a plasma and the sample inlet system is extremely long, so that the necessary volume of argon gas to be introduced into the plasma torch and consumed therein is great, up to about 10-20 l/min and power consumption is also great, up to 10-2 kw/h. Since argon gas is expensive, running costs become extremely high.

SUMMARY OF THE INVENTION

Accordingly, it is an object of the present invention to provide an improved emission analysis method using Inductively-Coupled Radio Frequency Plasma (ICP) and an improved apparatus for use in such a method so as to reduce running cost.

It is another object of the present invention to provide an improved emission analysis method using ICP and an improved apparatus for use in such method in such a manner that a plasma is maintained at a condition of a pilot light except for analyzing.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

According to a preferred embodiment of the present invention, an analyzing method which uses an Inductively-Coupled Radio Frequency Plasma (ICP) and an apparatus having a switch valve for switching the flow of a sample, the switch valve being interposed between a sample nebulizing chamber and a plasma torch, comprises the steps of: switching the switch valve to the side of the plasma torch only during the ICP analyzing period to introduce the sample into the plasma torch; supplying to an induction coil a first radio frequency source of electric power and supplying to the plasma torch a first volume of gas in such a condition that the sample introduced into the plasma torch is ionized as plasma; analyzing the plasma of the sample; switching the switch valve to an exit side so that the sample is removed during periods except for the ICP analyzing time; and supplying the induction coil a second radio frequency source of electric power and supplying to the plasma torch a second volume of gas in such a condition that the pilot light plasma is maintained in the plasma torch. The preferred embodiment also includes an apparatus for analyzing a sample using Inductively-coupled Radio Frequency Plasma including a plasma torch, an induction coil, a radio frequency voltage source for supplying electric power to the induction coil and a sample nebulizing chamber comprising a switch valve means being interposed between said nebulizing chamber and the plasma torch, a switching means for switching said switch valve means to a side of said plasma torch only during analyzing periods to introduce the sample into said plasma torch and a controller means for controlling said radio frequency voltage source and gas supply volume for the plasma torch in such a condition that pilot light plasma is maintained in said plasma torch during the period except for the analyzing periods.

BRIEF DESCRIPTION OF THE DRAWINGS

The present invention will become more fully understood from the detailed description given hereinbelow and the accompanying drawings which are given by way of illustration only, and thus are not limitative of the present invention and wherein:

FIG. 5 is a flow chart showing the operation of the ICP of FIG. 1.

DESCRIPTION OF THE PREFERRED EMBODIMENT

Figure 1:
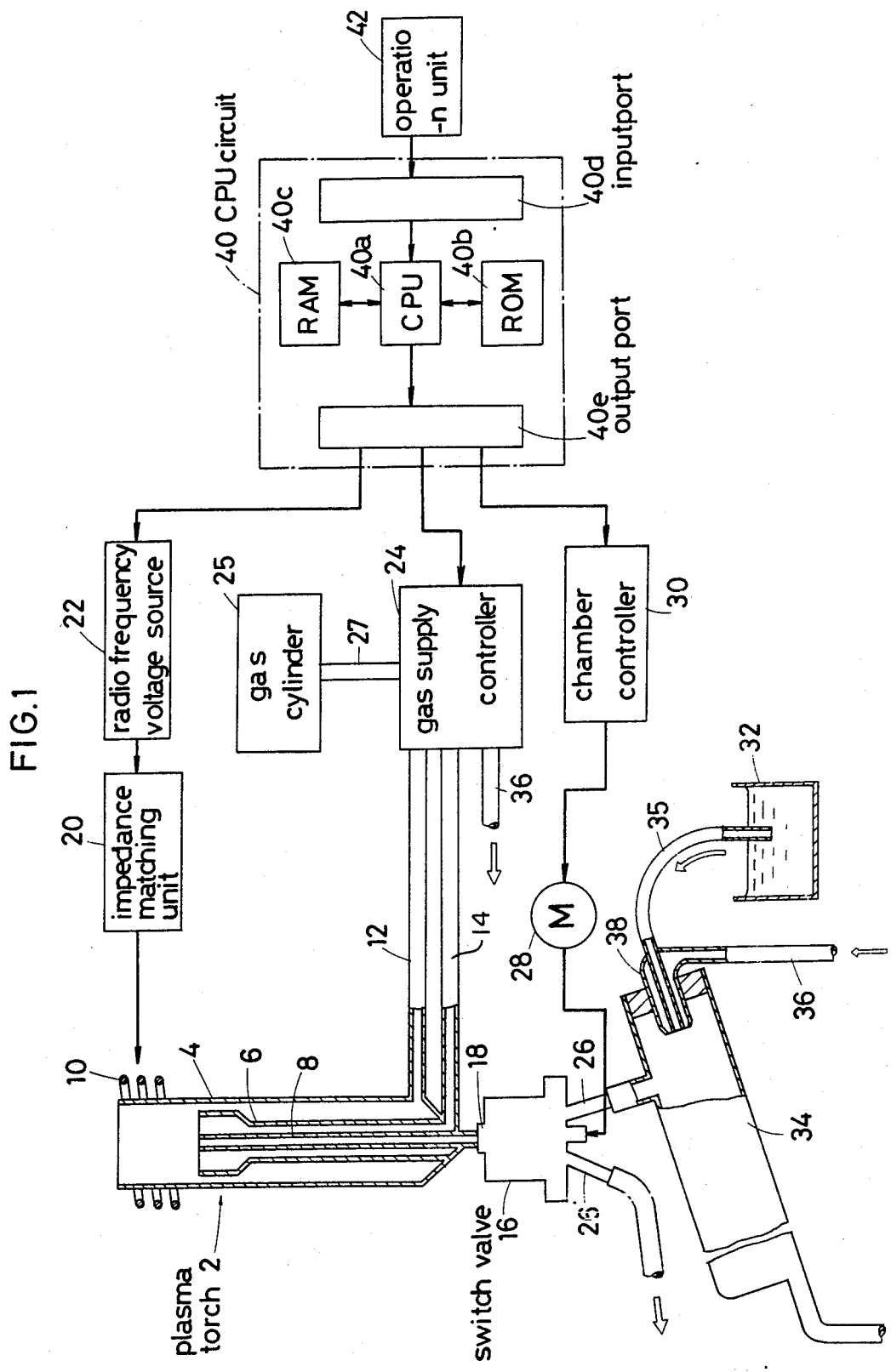
FIG. 1 shows a construction of an Inductively-Coupled Radio Frequency Plasma (ICP) apparatus according to the present invention wherein its mechanical elements are partially broken and electrical elements are designated in a block diagram.

FIG. 1 shows a construction of an Inductively-Coupled Radio Frequency Plasma (ICP) according to the present invention.

A plasma torch 2 comprises an external type 4, first and second inner tubes 8 which are double at the inner portion of the external tube 4. An induction coil 10 is turned at the top of the plasma torch 2 in order to generate a radio frequency magnetic field. A coolant gas (Argon gas) inlet tube 12 is provided at an opening formed at the lower portion of the external tube 4. At an opening formed at the lower portion of the first inner tube 6, a plasma gas (Argon gas) inlet tube 14 is connected. The lower end of the second inner tube 8 is extruded out of an opening of the external tube 4, so that the extruded end of the second inner tube 8 is connected to an exit port 18 of a switch valve 16.

The induction coil 10 is coupled to a radio frequency voltage source 22 via an impedance matching unit 20. The radio frequency voltage source 22 supplies the induction coil 10 radio frequency power, so that the induction coil generates a radio frequency magnetic field around the plasma torch 2.

The coolant gas inlet tube 12 and the plasma gas inlet tube 14 are connected to a gas supply control unit 24. The switch valve 16 has the exit port 18 and two inlet ports, one of which is an exit port 26' and the remaining is an inlet port 26 for a gas mixture between solution samples and carrier gas.

As will be described with reference to FIGS. 2 and 4, the switch valve 16 comprises a rotation member rotated by a pulse motor 28, so that the inlet port 26 for the mixture gas and the exit port 26' are connected together during a waiting condition except for an analyzing period while the inlet port 26 for the mixture gas and the exit port 18 are connected together during the analyzing period. Responsive to a pulse motor driving signal provided by a chamber controller 30, the pulse motor 28 drives the rotation member of the switch valve 16.

The ICP system also comprises a solution sample container 32, a sample nebulizering chamber 34, a solution sample absorbing tube 35, a carrier gas (Argon gas) inlet tube 36, and a nebulizer 38. The carrier gas inlet tube 36 is connected to the gas supply controller 24.

A central processing unit (CPU) circuit 40 comprises a microcomputer including a CPU 40a, a read only memory (ROM) 40b for storing an operation program as shown in the flow chart of FIG. 5, and a random access memory (RAM) 40c for storing data for access, an input port 40d for inputting an operation signal from an operation unit 42 to the CPU 40a, and an output port 40e for outputting the signal from the CPU 40a into the radio frequency power source 22, the gas supply controller 24, and the chamber controller 30.

The CPU circuit 40 provides a low power driving signal to the radio frequency power source 22 during a waiting condition except for an analyzing period while it provides a high power driving signal to the power source 22 during the analyzing period.

The CPU circuit 40 provides the gas supply controller 24 with a gas supply amount control signal. The gas supply controller 24 comprises a processing circuit responsive to the gas supply amount control signal and a valve driving section responsive to the processing circuit for switching on and off valves for the inlet tubes 12, 14, and 36. The gas supply controller 24 is connected to a gas cylinder supplying the coolant gas, the plasma gas, and the carrier gas, via a gas supply tube 27.

The CPU circuit 40 provides the chamber controller 30 a chamber control signal, so that responsive to the chamber control signal, the chamber controller 30 provides the pulse motor 28 with a pulse motor driving signal to drive it.

Figure 2:
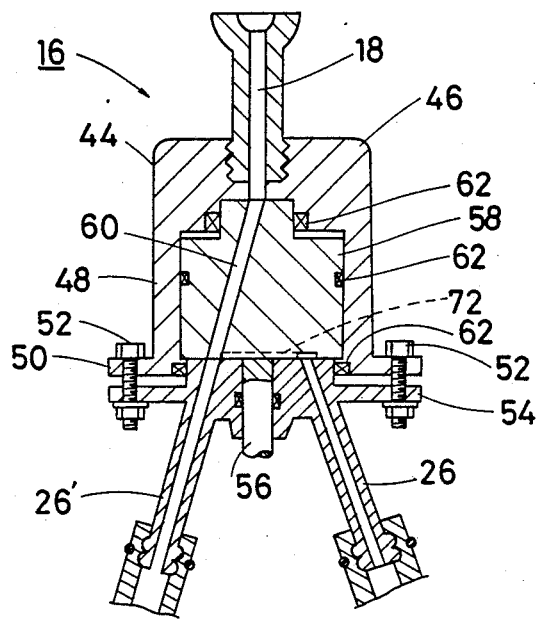
FIG. 2 is a cross-sectional view of a switch valve included within the ICP of FIG. 1.

FIG. 2 is a cross-section view of the switch valve 16. It comprises a cylindrical casing 44. At a top wall 46 of the casing 44, the exit port 18 to which the second inner tube 8 in the plasma torch 2 is connected is disposed by screwing. A flange 50 is formed at the circumference of the lower side of a side wall 48 of the casing 44. A lid 54 is secured on the casing 44 through a pair of bolts 52 at the flange 50. A rotation axis 56 of the pulse motor 28 is inserted into the lid 54 to form four inlet ports 26. At the inner space defined by the casing 44 and the lid 54, a rotation member 58 is stored which is connected to the rotation axis 56 of the pulse motor 28 and rotated by the driving of the pulse motor 28. Passing through the rotation member 58, a path 60 is provided in the rotation member 58. The top end of the path 60 is connected to the exit port 18 while the bottom end is connected to the inlet port 26. A seal material 62 is provided.

Figure 3:
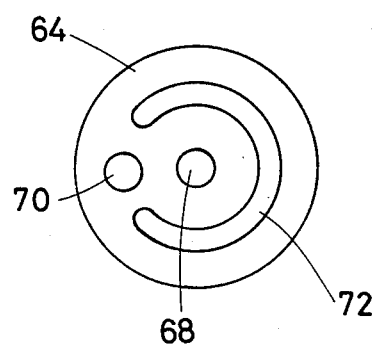
FIG. 3 is a plan view of a slide face by a rotation member in the switch valve.

FIG. 3 is a plan view of a slide surface 64 on which the rotation member 58 is slid as opposed to the lid 54. FIG. 4 is a plan view of a surface 66 opposed to the slide surface 64, viewing from the side of the lid 54.

As shown in FIG. 3, the slide surface 64 of the rotation member 58 includes a hole 68 at the center in which the rotation axis 56 of the pulse motor 28 is inserted. Along a circle with some radius around the hole 68, a bottom end 70 of the path 60 is positioned while along the same circle a circle groove 72 is formed over approximately three-fourths of the circle.

Figure 4:
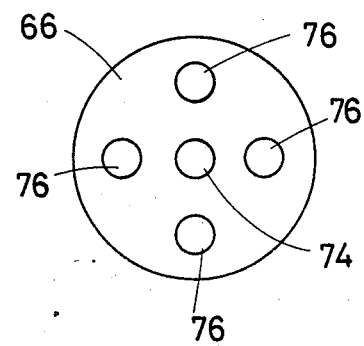
FIG. 4 is a plan view of a face opposed to a lid member in the switch valve.

As shown in FIG. 4, an opening 74 is provided at the center of the surface 66 opposed to the lid 54. The rotation axis 56 of the pulse motor 28 is inserted into the opening 74. Around the opening 74 and with the same radius as the circle in FIG. 3, four openings 76 are positioned with the right angles approximately for connecting the four inlet ports 26. When the pulse motor 28 is driven, the rotation member 58 coupled to the rotation axis 56 of the pulse motor 28 is rotated. When the bottom end 70 of the path 60 of the rotation member 58 is confronted with one of the four openings 76 connected to the inlet ports 26 of the lid 54, the gas mixture from the inlet port 26 is supplied into the plasma torch 2 through the path 60 of rotation member 58 and the exit port 18.

On the other hand, when one of the four openings 76 connected to the inlet port 26 of the lid 54 is confronted with the circle groove 72 on the rotation member 58, the gas mixture from the inlet port 26 exits into the exit port 26' through the circle groove 72.

FIG. 5 is a flow chart of the operation of the ICP system according to the present invention.

When a program starts, the CPU 40a of the CPU circuit 40 determines whether the operation unit 42 inputs a signal for ICP analyzing instruction (step n1). When it is detected that no such instruction signal is provided (NO) and that it is a waiting condition, a first chamber control signal is outputted into the chamber controller 30 via the output port 40e (step n2). Responsive to the first chamber control signal, the chamber controller 30 outputs a driving signal to the pulse motor 28, so that the inlet port 26 and the exit port 26' of the lid 54 are connected through the circle groove 72 of the rotation member 58 by driving the pulse motor 28. The pulse motor 28 is therefore driven to rotate the rotation member 58 engaged with the rotation axis 56 of the pulse motor 28. Thus, the inlet port 26 and the exit port 26' of the lid 54 are coupled to each other through the circle groove 70.

The CPU 40a of the CPU circuit 40 provides a low electric power control signal to the radio frequency voltage source 22 (step n3). The radio frequency voltage source 22 provides a low power, related to the low electric power control signal, to the induction coil 10 via the impedance matching unit 20. For example, the low electric power is about 100 w/h.

Further, the CPU 40a provides a first gas supply control signal to the gas supply controller 24, so that the total gas to be supplied to the plasma torch 2 should be a predetermined amount, for example, about 1.5 l/min by controlling the opening of an inner valve (step n4). Responsive to the first gas supply control signal, the gas supply controller 24 controls the inner valve so as to limit the total gas supplied by the gas cylinder 25 into the predetermined amount.

With steps n2-n4 (collectively referred to as a common step M), the waiting condition except for the ICP analyzing period is placed in which the plasma torch 2 is in the condition of a pilot light to thereby reduce consumption of power from the radio frequency voltage source 22.

In case it is detected in step n1 that the ICP analyzing period is selected (YES), the program is advanced to step n5. the operation of step n5 is identical with that of step M. In step n5, the plasma torch 2 is maintained in the condition of the pilot light and the switch valve 16 is in a position for expelling the sample.

After step M, to stabilize the sample entry system comprising the nebulizer 38 and the sample nebulizing chamber 34, the CPU 40a provides a signal enabling the solution sample and the carrier gas to be mixed in the nebulizer 38 and the gas mixture to be nebulized within the sample nebulizing chamber 34 (step n6). Then, a timer starts to count about 2-3 minutes during which the nebulizing condition is continued (steps n7 and n8). When the time counting is up, step n9 is selected to reset the timer. The CPU 40a provides a high electric power control signal into the radio frequency voltage source 22 via the output port 40e, so that the power from the radio frequency voltage source 22 subsequently increases up to about 1.2 kw/h, for example (step n10), and simultaneously provides a second gas supply control signal to the gas supply controller 24 (step n11).

Responsive to the second gas supply control signal, the gas supply controller 24 controls the increasing opening of the inner valve, so that the total gas supplied into the plasma torch 2 becomes a predetermined volume, for example, about 15 l/min (step n11). Step n12 is then selected to start a timer counting the time when with these steps the radio frequency voltage source 22 can output high power of about 1.2 kw/h and the gas supply controller 24 can output the volume of gas about 15 l/min. That is, the timer counts before the sample entry system can be stabilized. Step n13 is operated to detect that the time counting is up, and step n14 is operated to reset the timer.

Because, under the circumstances, the plasma suffices to ionize the sample, the CPU 40a outputs a second chamber control signal into the chamber controller 30 (step n15). Responsive to the second chamber control signal, the chamber controller 30 drives the pulse motor 28, so that the pulse motor 28 rotates the rotation member 58 in the switch valve 16. The inlet port 26 of the switch valve 16, the path 60, and the outlet port 18 are then connected, so that the sample within the sample nebulizing chamber 34 is introduced into the plasma torch 2. The introduced sample is ionized in the plasma torch 2.

Step n16 is selected to analyze the sample. Step n17 is selected to determine whether analysis has been completed. Upon completion, step n18 is selected to perform the operation similar to that of step M.

As described above, in accordance with the present invention, in the remaining conditions except for analysis the plasma torch 2 is kept in condition of a pilot light, so that the gas entry volume and electric power to be supplied to and consumed in the plasma torch 2 can be reduced to one tenth or less as compared to the conventional case. Thus, the running cost of the ICP analysis can be reduced much.

It is preferred that the impedance of the load in the radio frequency voltage source 22 should be matched with that of the plasma torch 2 to eliminate reflection loss and keep the precision of analysis. According to the present invention, it takes about 10-20 sec to enable the plasma torch 2 to analyze the sample. Without impedance matching and with generating reflection wave, the ICP analysis may be possible to simplify analysis operation.

While only certain embodiments of the present invention have been described, it will be apparent to those skilled in the art that various changes and modifications may be made therein without departing from the spirit and scope of the present invention as claimed.

What is claimed is:

1. A method for analyzing a plurality of samples using Inductively-Coupled Radio Frequency Plasma (ICP), wherein said method employs an apparatus comprising a plasma torch means for supplying a pilot light plasma and for receiving a coolant gas supply; an induction coil disposed around the top of said plasma torch means for generating a radio frquency magnetic field; a radio frequency voltage source connected via an impedance matching unit means to said induction coil for supplying electric power thereto; and a switch valve means operatively connected to said plasma torch means wherein said switch valve means introduces said plasma torch means in a first position during an ICP analysis period, and said switch valve means prevents said sample from entering said plasma torch means in a second position; said method comprising the steps of:
   switching said switch valve means to said first position only during said ICP analysis period so as to introduce said sample into said plasma torch means;
   supplying said induction coil with a first volume of coolant gas in such a manner that said sample is introduced into said plasma torch means in the form of ionized plasma;
   analyzing said plasma of said sample;
   switching said switch valve means to said second position during periods except for said ICP analysis period;
   supplying said induction coil with a second radio frequency source of electric power and supplying said plasma torch means with a second volume of gas in such a manner that said pilot light plasma is maintained in said plasma torch means; and repeating the above steps, wherein the volume of electric power and gas consumed by said apparatus when said switch valve is in said second position is reduced from that consumed in said first position so as to reduce running costs for analyzing a plurality of samples.

2. The method as set forth in claim 1, further comprising the step of counting for a first counting period between said first switching step and said first supplying step so as to allow said sample to stabilize in said plasma torch means.

3. The method as set forth in claim 2, further comprising the step of counting for a second counting period between said first supplying step and said analyzing step so as to provide for a suitable condition for forming plasma in said plasma torch means.

4. The method as set forth in claim 1, wherein the ratio of said first radio frequency source of electric power to said second radio frequency source of electric power, and the ratio of said first volume of gas to said second volume of gas are both about one to ten.

5. An apparatus for analyzing a plurality of samples using Inductively-Coupled Radio Frequency Plasma (ICP) which comprises:
   a plasma torch means for supplying a pilot light plasma and for receiving a coolant gas supply,
   an induction coil disposed around the top of said plasma torch means for generating a radio frequency magnetic field,
   a radio frequency voltage source connected via an impedance matching unit means to said induction coil for supplying electric power to said induction coil,
   a switch valve mans operatively connected to said plasma torch, wherein said switch valve means introduces said sample into said plasma torch in a first position during an ICP analysis period, and said switch valve means prevents said sample from entering said plasma torch means in a second position,
   a switching means for switching said switch valve means to said first position only during said ICP analysis period,
   a sample nebulizing chamber operatively connected to said switch valve means for introducing said sample into said switch valve means, and
   a controller means operatively associated with said plasma torch and said induction coil for controlling said radio frequency voltage source and said coolant gas supply for said plasma torch in such a condition that said pilot light plasma is maintained in said plasma torch during periods except for said ICP period analysis period, wherein the volume of electric power and gas consumed by said apparatus when said switch valve is in said second position is reduced from that in said first position so as to reduce running costs for analyzing a plurality of samples.

6. An apparatus as defined in claim 5, wherein said switch valve means comprises:
   a casing,
   an upper port operatively connected between said casing and said plasma torch, and formed in an upper part of said casing for introducing said sample into said plasma torch,
   a rotation member rotatably mounted within said casing, said rotation member having a plasma torch introduction conduit formed therethrough, wherein an upper portion of said introduction conduit aligns with said upper port, said rotation member being rotated by said switching means,
   a lower lid operatively connected to a lower part of said casing and to said sample nebulizing chamber, said lower lid having a plurality of lower lid ports formed therein,
   wherein said switching means rotates said rotation member so that said switch valve means is in said first position and so that said introduction conduit aligns with one of said lower lid ports; and wherein said switching means rotates said rotation member so that said switch valve means is in said second position, said introduction conduit is not aligned with said lower lid port, and said sample bypasses said introduction conduit by flowing into a first lower lid port and out of a second lower lid port out of a second lower lid port.

7. An apparatus as defined in claim 6, wherein a lower portion of said rotation member includes a circular groove for a bypass path for said sample from said introduction conduit so that said sample flows into a first lower lid port and out of a second lower lid port when said switch valve means is in said second position.

* * * * *